United States Patent
Badia Segura (10) Patent No.: US 6,641,574 B2
(45) Date of Patent: Nov. 4, 2003

(54) CONNECTING DEVICES FOR CATHETERS, PERFUSION EQUIPMENT AND SYSTEMS FOR PERFUSING OR DRAINING LIQUIDS IN THE HUMAN BODY

(76) Inventor: Marcelo Badia Segura, Bruch, 61, Pral., Barcelona (ES)

( * ) Notice: Subject to any disclaimer, the term of this patent is extended or adjusted under 35 U.S.C. 154(b) by 0 days.

(21) Appl. No.: 09/998,562

(22) Filed: Nov. 30, 2001

(65) Prior Publication Data

US 2002/0038114 A1 Mar. 28, 2002

Related U.S. Application Data

(63) Continuation of application No. PCT/ES00/00199, filed on Jun. 2, 2000.

(30) Foreign Application Priority Data

Jun. 4, 1999 (ES) ................................................ 9901227

(51) Int. Cl.⁷ ............................................. A61M 25/16
(52) U.S. Cl. ....................................... 604/533; 604/534
(58) Field of Search ............................. 604/533, 94.01, 604/171, 173, 175, 263, 523, 534, 535, 905

(56) References Cited

U.S. PATENT DOCUMENTS

| | | | | |
|---|---|---|---|---|
| 3,469,579 A | * | 9/1969 | Hubert | 604/533 |
| 4,187,848 A | * | 2/1980 | Taylor | 604/243 |
| 4,844,512 A | * | 7/1989 | Gahwiler | 285/275 |
| 5,137,524 A | * | 8/1992 | Lynn et al. | 604/414 |
| 5,139,483 A | * | 8/1992 | Ryan | 604/533 |
| D380,262 S | * | 6/1997 | Van Funderburk et al. | |
| 5,941,853 A | * | 8/1999 | Collins | 604/158 |
| 6,096,011 A | * | 8/2000 | Trombley et al. | 251/149 |

* cited by examiner

*Primary Examiner*—Brian L. Casler
*Assistant Examiner*—Kevin C. Sirmons (57) ABSTRACT

The invention comprises an assembly of two external enveloping bodies, open at one end by which they can be coupled to one another so as to slide to a releasable holding position of said enveloping elements, which enveloping elements have, at the opposing ends, respective connections to enable them to communicate with a container or containers containing the liquids to be perfused or to be drained and a connection for the element for perfusion to the patient, said enveloping bodies also having, in their interior, couplable means intended to allow the passage of liquid to be perfused from the inlet conduit to the outlet conduit communicating with the catheter or other perfusion device.

6 Claims, 10 Drawing Sheets

FIG. 3 BIS

FIG. 4 BIS

CONNECTING DEVICES FOR CATHETERS, PERFUSION EQUIPMENT AND SYSTEMS FOR PERFUSING OR DRAINING LIQUIDS IN THE HUMAN BODY

CROSS-REFERENCE TO RELATED APPLICATIONS

This application is a continuation of International Application No. PCT/ES00/00199 filed Jun. 2, 2000, which claims the benefit of priority based upon Spanish Patent Application No.9901227 filed Jun. 4, 1999, the entire disclosures of which are incorporated herein by reference.

FIELD OF THE INVENTION

The present invention relates to some improvements made in connecting devices for catheters, perfusion equipment and systems for perfusing liquids to the human body or for draining them from it.

BACKGROUND OF THE PRIOR ART

CH 674944 discloses a device for the connection of conduits for medical liquids to the body of a patient comprising two parts with connectors to be engaged together both having internal protrusions in form of tubes for the conduction of the perfusion liquid, which are engageable together upon the assembly of both parts of the device.

OBJECT OF THE INVENTION

The object of the present invention, in particular, is to avoid contamination by direct and indirect contact between the elements of the connection and similarly to avoid contamination by aspiration of air or liquids from the exterior, which constitutes a problem in currently known connecting devices.

A further object of the present invention is to obtain a connection for catheters, perfusion equipment and the like for perfusing liquids to patients which is of a universal type and is applicable to normal catheters, thicker catheters for haemodialysis, urethral probes and the like.

SUMMARY OF THE INVENTION

In general, an object of the present invention is to enable the connection to be used in any type of catheter or the like.

To achieve the aforementioned objects, the connection forming the subject of the present invention is characterised in that it comprises two hollow, preferably cylindrical, external enveloping bodies which are coupled so as to slide one within the other, the bodies being open at the connected ends and having tubes for connection to the catheter or to the perfusion container respectively at the other ends. It can also be used with currently known catheters with appropriate connections at the ends. One characteristic of the present invention is that the couplable or plug-in tubes forming the body of the connection have respective internal elements which can be connected by the introduction of said external bodies one within the other, allowing the inlet from the perfusion liquid-carrying container to be connected to the outlet connected to the catheter.

For the objects of the present invention it is important that the radial distance between the external body and the internal body is considerable to prevent capillary action phenomena and, in general, that there is a path which is as long as possible between the point of union between the external bodies and the point of contact, in other words of union of the internal bodies with the result that the route of possible contamination is as long as possible, thus making it difficult for contamination to arrive at the internal connection. At the appropriate time, when the integral parts of the connection are given a considerable length, the distance between the open edges of the external body and the corresponding internal edges can simultaneously be sufficiently great to avoid manual contact during handling of the connection.

To lengthen the route of contamination, the present invention proposes the optional production of ribs or grooves in the course of said route of possible contamination, for example at the external surface of the corresponding internal element or body. It is obvious that said assemblies of ribs or grooves could also be arranged at the external surface of the internal body which remains inside the connection once the connection has been made.

The present invention will be applicable to any type of internal union of the tubes and, similarly, will be applicable to the aspiration of air and to the passage of liquids.

The new connection can be applied to the outlets of flasks, syringes, bottles or in any other suitable element.

The releasable internal connection can be produced by two tubular elements respectively fixed to each of the two external enveloping bodies which can be coupled in a sliding manner so that, when one is introduced into the other in a sliding manner, the internal tubular elements are coupled by the congruence of their ends, for example, by means of a taper of one of the tubular elements fixed in an enlargement at the other end of the other tubular element.

Said connection for the passage of liquid can similarly be formed by internal fixed tubular elements which abut in register at their ends and have elastic joints to produce the necessary seal.

It is also feasible to arrange an internal tubular element in one of the external enveloping bodies and a needle in the other, which is coupled by passing through a spongy stopper for closing the fixed extension in the other external enveloping element or by means of a cylindrical nozzle which is threaded in a preformed aperture in said spongy stopper.

A characteristic common to the various embodiments of union of the internal tubular elements is that the external enveloping bodies which are coupled to one another in a sliding manner are provided with a coupling and holding region which is effective in the position at which one of the bodies is introduced into the other, having a coupling arrangement by means of ribs interposed in one another in the axial abutment position or alternatively by means of screw-threaded end regions for coupling said bodies one another or other similar systems for instance a bayonet fitting or a closure with an external thread and the like.

Between the enveloping bodies which can be coupled in a sliding manner there is an annular chamber round the region of coupling of said external bodies which will act as a chamber for receiving any impurities in the air or liquids originating from the exterior which might normally penetrate through the coupling regions. A complementary means can consist in the arrangement of a sleeve of felt or other material, optionally impregnated with disinfectant, which is arranged in one or other of the cylindrical elements which fit together in a sliding manner to block the gap existing between them.

BRIEF DESCRIPTION OF THE DRAWINGS

The accompanying drawings of embodiments of the present invention, given as non-limiting examples, will assist understanding.

FIGS. 3b and 4b are views similar to FIGS. 3 and 4 respectively with internal grooves to lengthen the route of contamination.

DETAILED DESCRIPTION OF THE INVENTION

As shown in the figures, the improvements in the present invention are applicable to a connecting device between a perfusion container and a catheter which is to be coupled to a patient's body, comprising, according to the invention, two external enveloping bodies 1 and 2 which are preferably cylindrical in shape, are open at one end and can be coupled one within the other in a sliding manner, the external enveloping bodies having, at the other ends, respective orifices 3 and 4 for coupling to said members, in other words administration of the product to be perfused and connection to the catheter. As mentioned hereinbefore, it can also be used with currently known catheters with the appropriate connections at the ends. For holding the external enveloping elements 1 and 2 in the fully introduced position, which is the operating position, as shown in FIGS. 2 to 6, there can be provided various devices which will be described hereinafter, and the various forms proposed for producing the coupling for the passage of fluids between the two external enveloping elements 1 and 2 in the interior of the hollow chamber defined by said hollow cylindrical enveloping bodies will also be described. The provision of radial separations between the tubular elements which make up the connection with values higher than those caused by the displacement of the liquid by capillary action will also be of great importance for maintaining the internal asepsis of the connection, but it should be taken into consideration that this effect may be particularly sensitive in view of the virtually horizontal position which said connections can adopt in actual use.

The body 2 will similarly have an air inlet 65 with an anti-bacterial filter.

Similarly, the bodies 1 and 2 are shown with gripping and handling wings indicated by the numerals 68 and 68', but it should be understood that said wings can be substituted by any other suitable means which perform the same function such as reeding, projecting arms, etc.

The various embodiments in FIGS. 1 to 6 show methods of connecting and holding the tubular elements 1 and 2 and will be described briefly.

Figure 1:
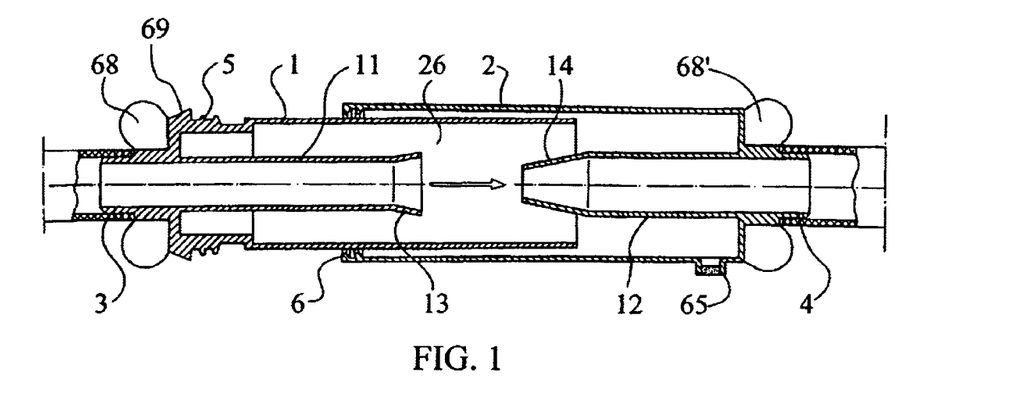
FIGS. 1 and 2 show a connection according to the present invention provided with plug-in internal tubular elements.
Figure 2:
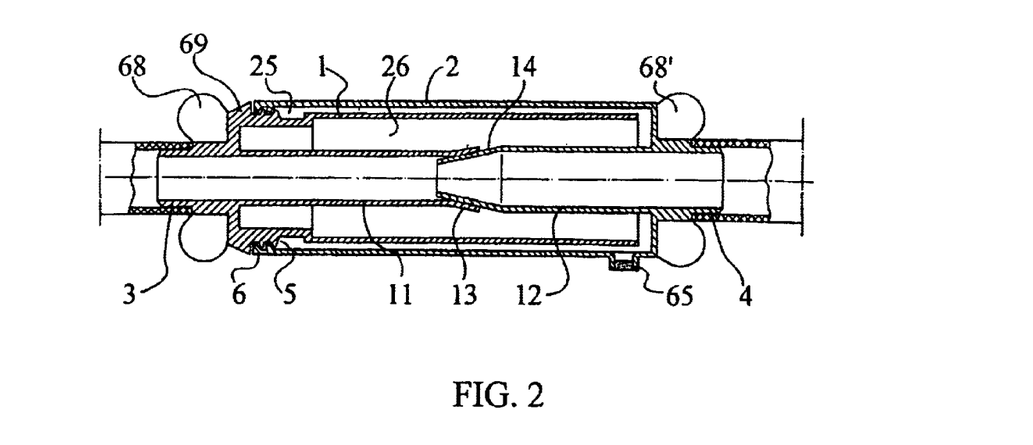

FIG. 1 shows the arrangement of a set of ribs 5 in the enveloping part 1 and a further set of interconnected ribs 6 in the interior of the open end of the part 2, which are congruent inside one another as shown in FIG. 2, holding the two elements together.

Figure 4:
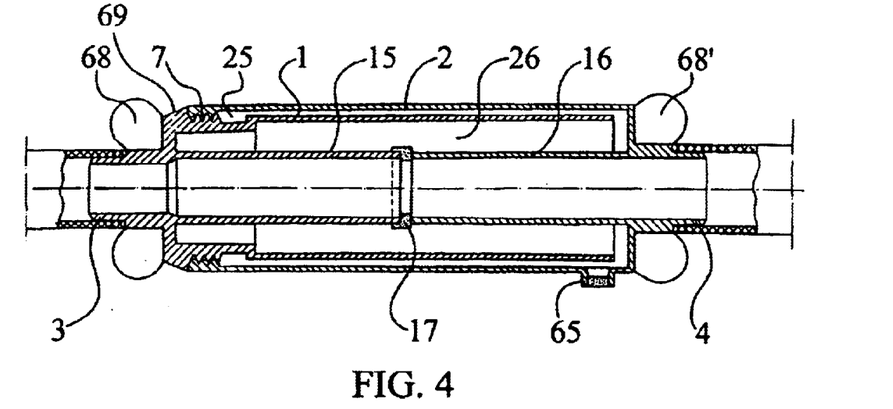
FIG. 4 shows a section of a connection in which the internal elements are formed by completely coupled cylindrical parts with an intermediate elastic joint.

As shown in FIG. 4, the coupling can be produced by means of the threaded regions indicated by the numeral 7 which will replace the sets of ribs 5 and 6 of the external enveloping elements.

Figure 5:
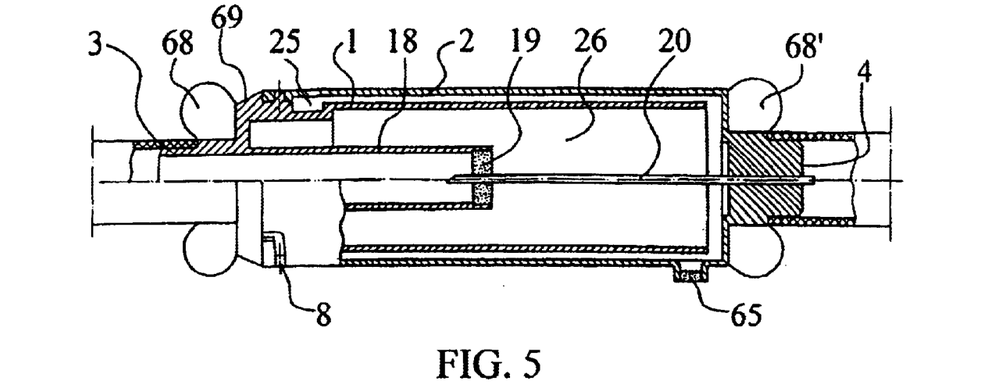
FIG. 5 shows an embodiment in which the internal connection between the constituent bodies of the connection is produced by means of a needle which perforates a spongy stopper.

FIG. 5 shows a configuration in which the coupling of the external enveloping elements 1 and 2 is achieved by means of a bayonet system 8.

Figure 6:
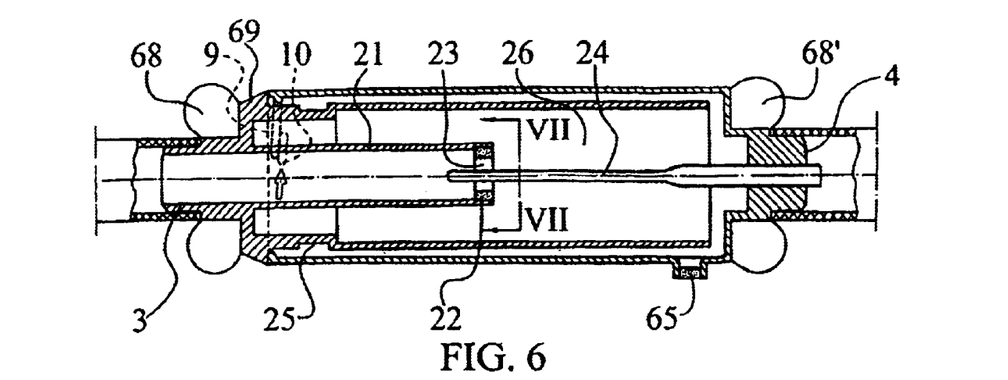
FIG. 6 shows an embodiment in which the connection between the two cylindrical elements is produced by introducing a fixed cannula into one of the two cylindrical bodies coupled in a sliding manner in a preformed groove in a spongy stopper mounted in the other cylindrical coupled part.
Figure 7:
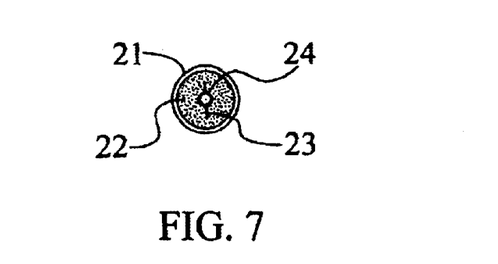
FIG. 7 is a cross-section through the plane indicated in FIG. 6.

FIG. 6 shows a form of coupling which comprises a helical half spiral 9 and corresponding stop 10 for holding by latching.

It will be appreciated that the embodiments shown merely serve as an illustration, and that said coupling can be produced by many other devices.

The coupling of the internal elements which allow the passage of the fluid can similarly be produced in various ways, as shown in the various embodiments which will be described briefly hereinafter.

Figure 3:
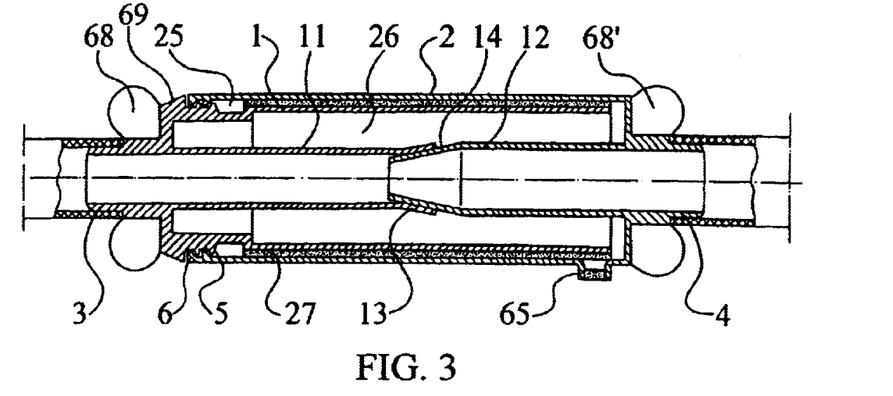
FIG. 3 shows a longitudinal section of a connection similar to those in FIGS. 1 and 2 with a covering of felt or other material, optionally impregnated with disinfectant in the gap between the two bodies which can be coupled in a sliding manner.

FIGS. 1 to 3 show a configuration comprising internal tubular extensions 11 and 12 associated with the external enveloping parts 1 and 2 respectively. The internal part 11 has an enlargement or flare 13 at one end while the part 12 has a narrowing conical portion—14—capable of mating with the enlargement 13, as shown in FIGS. 2 and 3.

FIG. 4 shows that the tubular elements 15 and 16 internally connected to the external enveloping elements 1 and 2 respectively are straight cylinders and are intended for coupling it completely with interposition of an elastic sealing joint 17.

The configuration in FIG. 5 shows the arrangement of an internal tubular extension 18 of the external enveloping element 1 which also carries a stopper or spongy closure element 19 at its end and a needle 20 coupled to the external enveloping element 1 which penetrates and passes through the spongy stopper 19.

In the configuration shown in FIG. 6, the internal enveloping element has a cylindrical tubular body 21 carrying, in its orifice, a spongy stopper 22 which is provided with a straight central incision 23 in which there can be inserted an external cannula 24 coupled internally to the external enveloping element 2.

Additionally to improve the characteristics of asepsis of the connection, the connection will have a chamber 25 formed between the internal and external enveloping bodies 1 and 2, for example by means of an offset produced in the region of the bottom of the enveloping body 1. It will be appreciated, however, that said annular chamber could be produced in many different forms providing that the desired object is achieved, in other words the provision of an intermediate chamber in the possible path for the admission of air from the exterior through the region of coupling of the parts 1 and 2 to the interior of the chamber 26 in which the connecting elements for passage of the liquid to be perfused are arranged.

Sealing joints can be incorporated at the union between the external bodies, for example at the beginning of the screw-threaded region 5, in particular could be supported on the flange 69, FIG. 1, existing at the beginning of said screw-threaded region.

To improve the conditions of asepsis, the length of the members making up the connection will be as great as possible, compatible with appropriate handling of the connection and, in particular, the path of contamination will be as long as possible between the point of contact between the external bodies, indicated by the connecting point between the reliefs 5 and 6 in FIG. 2 and the point of internal connection shown by the coupling cones between the internal elements 11 and 12. For this, it is possible to use the embodiment shown in FIG. 3b and 4b which show the production of grooved regions 66 at the external surface of the element 12', as shown in FIG. 3b, or a row of fine projecting ribs 67, like those shown in FIG. 4b for an internal element 12".

Similarly, to improve the seal from the exterior, it is possible to introduce a sheet of flexible, adaptable material such as felt or the like 27, FIG. 3, between the surfaces of the enveloping bodies 1 and 2, all this tending to obstruct the passage of possibly contaminated air or liquid from the exterior of the connection to the interior thereof. Said felt material could be replaced by a spongy material or a material of a different configuration optionally impregnated with the disinfectant.

The parts which are more or less critical with respect to the risk of contamination can also be distinguished visually by colours, for example red or green, insertion of coloured threads and other visible finishes. This distinction could also be made by means of various surface finishes which allow the critical parts of the connection to be distinguished clearly and in which physical contact with possibly contaminating elements must be avoided.

Figure 8:
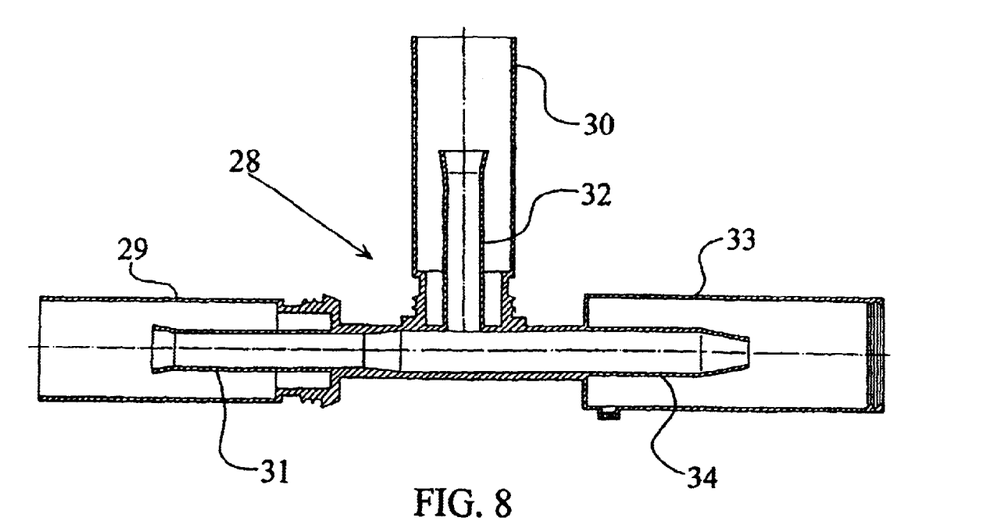
FIGS. 8 and 9 show respective schematic sections of connections of two and three inlet lines.

The connection forming the subject of the present invention could be applied to various configurations of supply of liquid to be perfused, said configurations essentially comprising the arrangement of multiple inlets such as double, triple or quadruple inlets, for example. FIG. 8 shows a unitary assembly 28 comprising two inlets for liquid to be perfused which, in a manner similar to that described hereinbefore, comprise external enveloping cylindrical bodies 29 and 30 with internal tubular elements 31 and 32 as well as an external enveloping body 33 for an internal tubular element with a cone-shaped end 34. In the configuration in FIG. 9, an integral part 35 can be seen with three combined inlets for liquid to be perfused, each of which is made up of a cylindrical enveloping body 36, 37 and 38 with internal connecting bodies of the type described hereinbefore, which converge at a single conduit 39 which will allow the connection to a catheter to be made using an arrangement similar to that described hereinbefore of the external enveloping body 40 and the internal connecting element 41.

The connection forming the subject of the present invention can also be applied to a syringe so that the body 2 will have a cone, not shown, for receiving it, allowing normal use of a syringe, for example extraction of blood, administration of antibiotics, etc.

Figure 10:
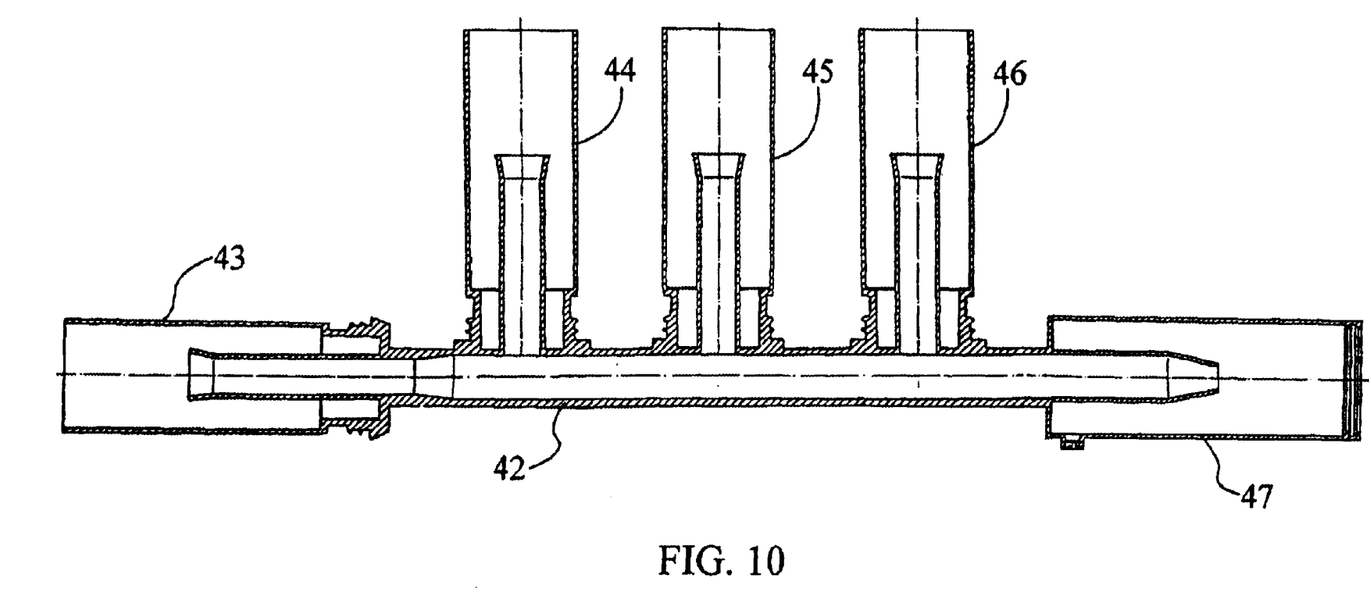
FIG. 10 shows a schematic longitudinal section of a connection between four lines in a linear arrangement.

FIG. 10 shows a quadruple linear connection in which there converge at a single supply duct 42 a first coaxial unit 43 formed by an external enveloping body and an internal connecting element and a further three connecting units of the type described hereinbefore, such as those indicated by the numerals 44, 45 and 46. A common connecting outlet 47 will allow the coupling to a catheter or further means of perfusion.

Figure 11:
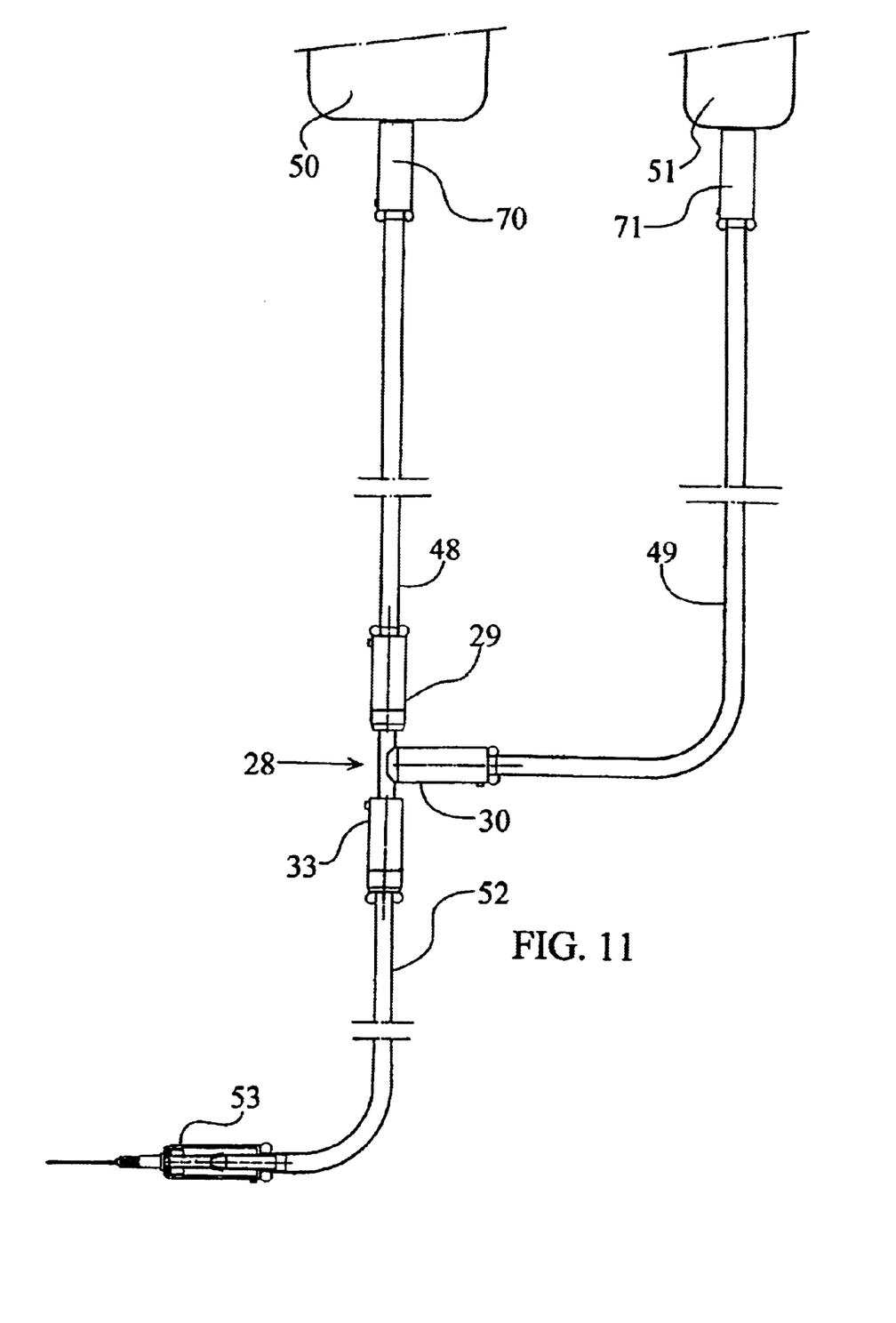
FIGS. 11, 12 and 13 show respective schematic views corresponding to connections of two, three and four inlet lines for use in appropriate bottles or flasks.
Figure 12:
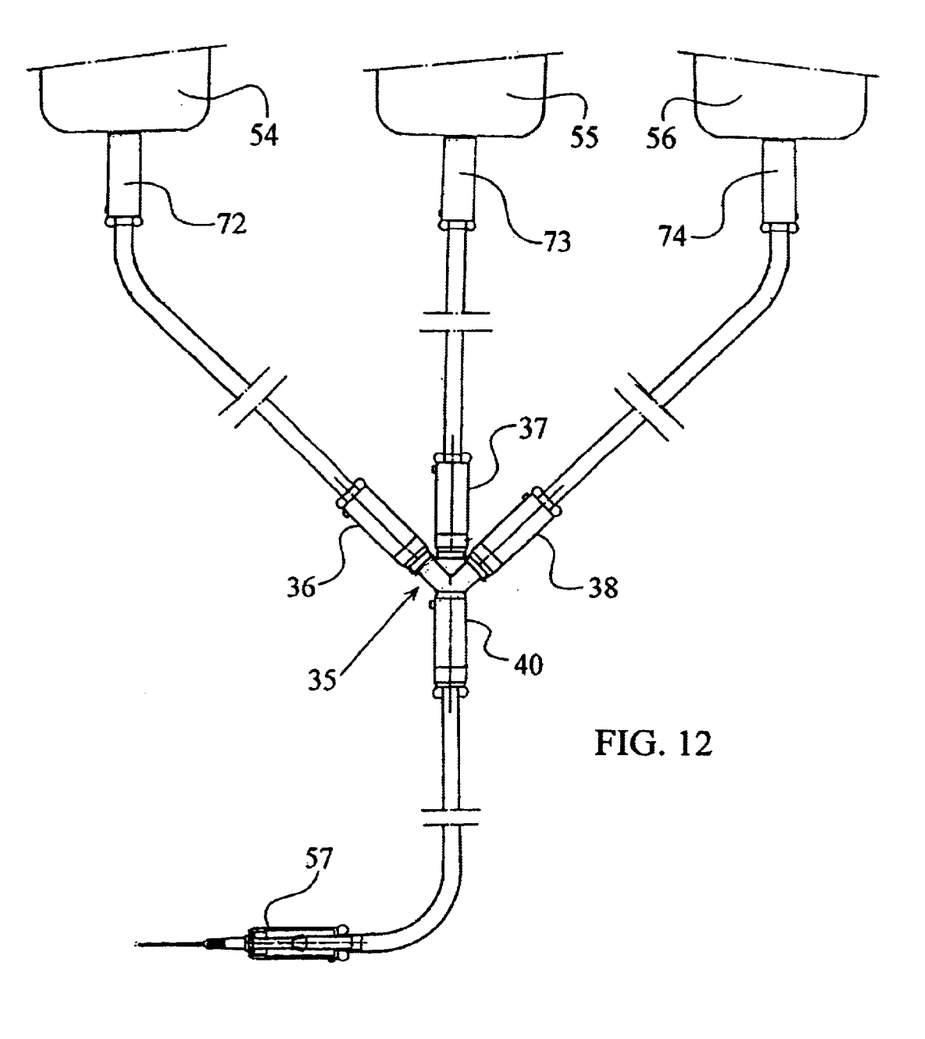
Figure 13:
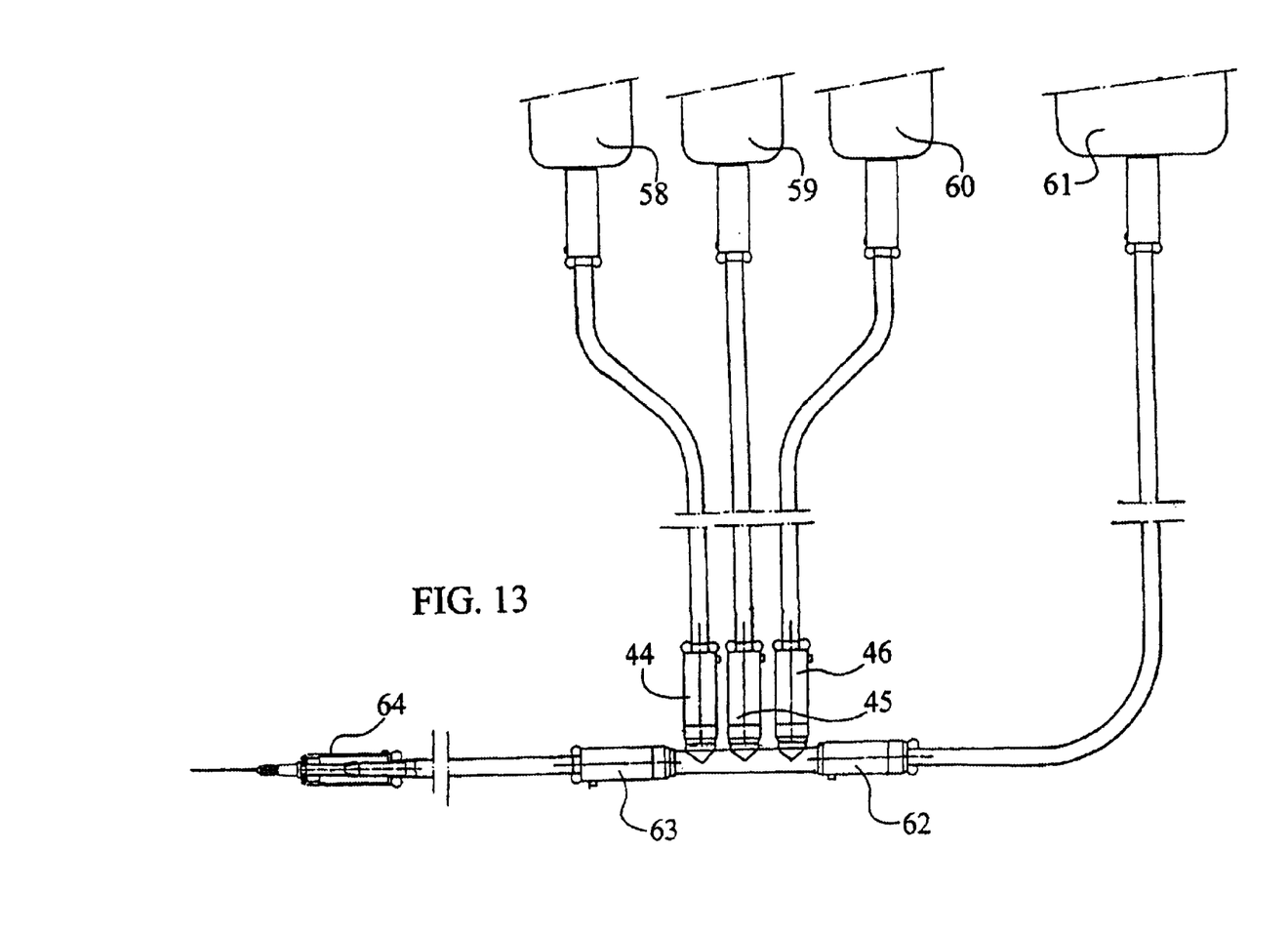

FIGS. 11, 12 and 13 show schematically arrangements corresponding to the multiple connections described hereinbefore. Thus, for example, an element 28 for double supply could be connected by means of the conduits 48 and 49 to the respective containers of perfusion liquid 50 and 51, with the same connecting devices forming the subject of the invention, indicated by the numerals 70 and 71 in FIG. 11, there being a single outlet conduit 52 to a catheter or further perfusion element 53.

The coupling terminals, for example the one indicated by the numeral 53, could be produced as in the present invention or with a traditional system such as the known "luer lock" or with any other appropriate system.

Figure 9:
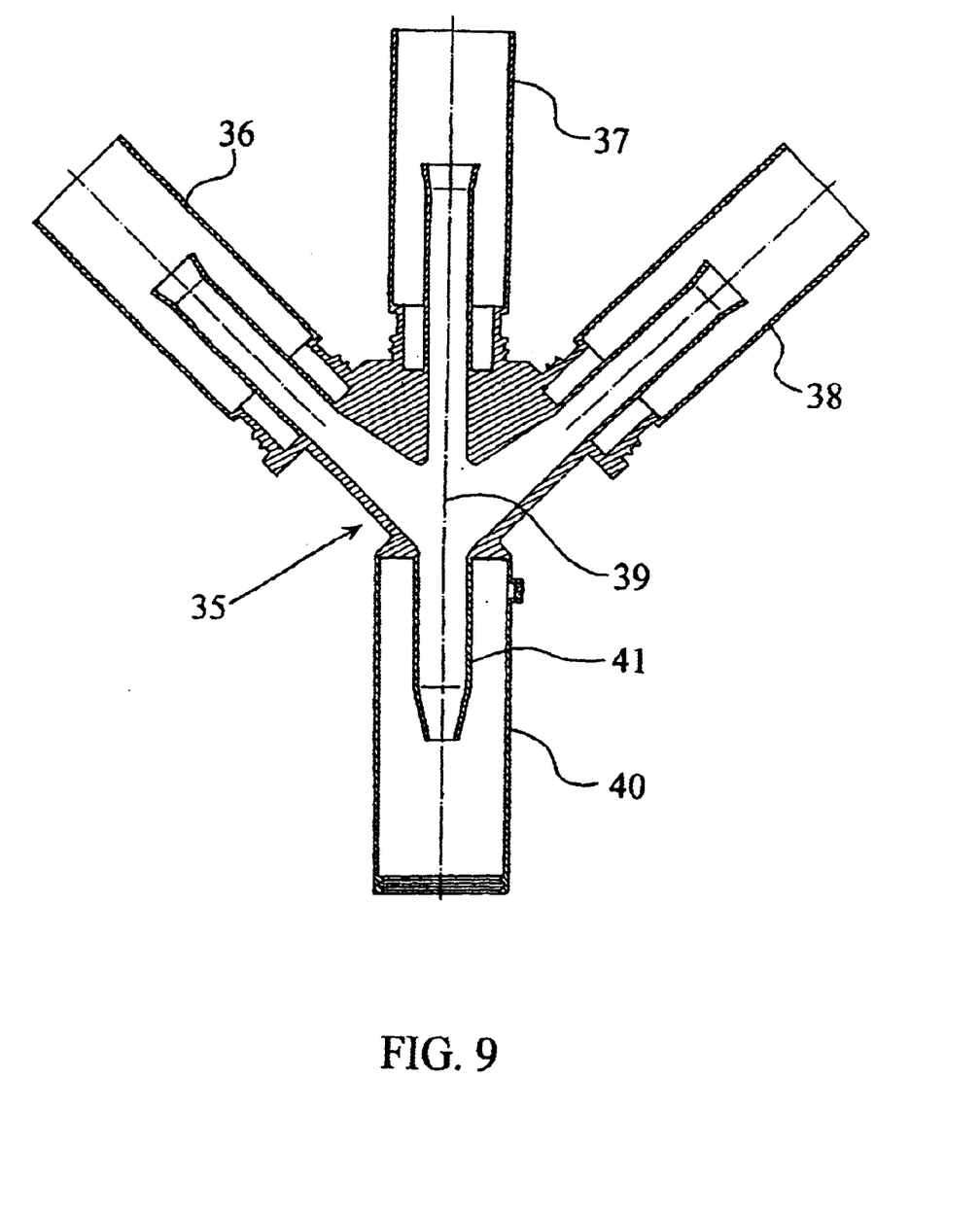

FIG. 12 shows a similar arrangement for a triple connecting element of the type 35 shown in FIG. 9, the connection being provided by the appropriate conduits 72, 73 and 74 to the supply containers 54, 55 and 56 supplying, by means of a single duct, the outlet connection 57 which can be coupled to a catheter or other similar element.

FIG. 13 shows the schematic arrangement of the quadruple supply assembly shown in FIG. 10, demonstrating that the inlet connections 44, 45 and 46 receive perfusion liquids from the containers 58, 59, 60, that they are added to those from the container 61 which supplies the coaxial inlet 62, there being a single outlet 63 for supplying the terminal 64 which can be coupled to a catheter or other similar element.

By making up elements which have been described, it is possible to produce connections to the human body for catheters or other perfusion elements which have much higher characteristics of asepsis than those currently known and which allow simple and effective handling.

What is claimed is:

1. A connecting device for catheters, perfusion equipment and systems for perfusing liquids to the human body, comprising an assembly of two external enveloping elements, open at one end by which they can be coupled to one another so as to slide to a reasonable holding position of said enveloping elements, which enveloping elements have, at the opposing ends, respective connections which are specific or adapted to existing catheters to enable them to communicate with a container or containers containing the liquids to be perfused and a connection for the element for perfusion to the patient, said enveloping elements also having, in their interior, couplable internal tubular elements intended to allow passage of liquid to be perfused from an inlet conduit to an outlet conduit communicating with a catheter or other perfusion device, with an arrangement of sealing means between the internal tubular elements and external enveloping elements to prevent the admission of contaminants originating from the surrounding environment, wherein a radial separation is formed between the external enveloping elements forming the connection, which is greater than that required to allow the displacement by capillary action of the liquid to be perfused and forms an intermediate chamber disposed in a path of passage of air from the exterior to the interior of the connection, and wherein one of the external enveloping elements has an air inlet with an anti-bacterial filter formed therein.

2. The connecting device for catheters according to claim 1, wherein the internal tubular elements of the external enveloping elements coincide completely at their opposing edges, with interposition of one or more sealing gaskets.

3. The connecting device for catheters according to claim 1, wherein the external enveloping elements are held in a completely coupled position by respective sets of external and internal ribs formed on the external enveloping elements which allow the external enveloping elements to be held with pressure.

4. The connecting device for catheters according to claim 1, wherein the external enveloping elements are held in a completely coupled position by a bayonet-type device.

5. The connecting device for catheters according to claim 1, wherein the connection for the passage of liquids by the internal tubular elements is made by a cylindrical extension of one of the external enveloping elements which has, at its connected end, an elastic stopper with a straight groove capable of receiving a cannula integral with the other of the external enveloping elements.

6. The connecting device for catheters according to claim 1, wherein critical connection elements have special visible colours and/or finishes to assist identification thereof and avoid contaminating contacts.

* * * * *